US008367868B2

(12) United States Patent  
Bertolini et al.

(10) Patent No.: US 8,367,868 B2  
(45) Date of Patent: Feb. 5, 2013

(54) PROCESS FOR THE SYNTHESIS OF ARYLOXYPROPYLAMINE AND HETEROARYLOXYPROPYLAMINE

(75) Inventors: Giorgio Bertolini, Milan (IT); Barbara Verzola, Paderno D'adda (IT); Domenico Vergani, Biassono (IT)

(73) Assignee: Archimica S.r.l., Milan (IT)

( * ) Notice: Subject to any disclaimer, the term of this patent is extended or adjusted under 35 U.S.C. 154(b) by 625 days.

(21) Appl. No.: 12/444,710

(22) PCT Filed: Oct. 4, 2007

(86) PCT No.: PCT/EP2007/060564
§ 371 (c)(1),
(2), (4) Date: Apr. 8, 2009

(87) PCT Pub. No.: WO2008/046745
PCT Pub. Date: Apr. 24, 2008

(65) Prior Publication Data
US 2010/0105942 A1    Apr. 29, 2010

(30) Foreign Application Priority Data

Oct. 16, 2006 (IT) .............................. MI2006A1987

(51) Int. Cl.
*C07C 209/14*    (2006.01)
(52) U.S. Cl. ............. 564/305; 560/30; 560/31; 564/102
(58) Field of Classification Search ................. 564/305, 564/102; 560/31, 30
See application file for complete search history.

(56) References Cited

U.S. PATENT DOCUMENTS

| | | | |
|---|---|---|---|
| 4,018,895 A | 4/1977 | Molloy et al. | |
| 4,314,081 A | 2/1982 | Molloy et al. | |
| 4,902,710 A * | 2/1990 | Foster et al. | 514/438 |
| 5,238,959 A | 8/1993 | Robertson et al. | |

FOREIGN PATENT DOCUMENTS

| | | |
|---|---|---|
| EP | 0 534 756 A2 | 3/1993 |
| WO | WO 00/58262 A1 | 10/2000 |
| WO | WO 01/62704 A1 | 8/2001 |

OTHER PUBLICATIONS

J. March, Advanced Organic Chemistry: Reactions, Mechanisms and Structure, (1985) 3rd ed., John Wiley & Sons, pp. 370, 382.*
Protective Groups in Organic Synthesis, Chapter 7, Third Edition, 1999, Wiley-Interscience, pp. 494-653.
Bhandari, K. et al., *Biochemical and Medicinal Chemistry* 2005, vol. 13, pp. 1739-1747 XP002460761.

* cited by examiner

*Primary Examiner* — Johann Richter
*Assistant Examiner* — Pancham Bakshi
(74) *Attorney, Agent, or Firm* — ProPat, L.L.C.

(57) ABSTRACT

The present invention relates to a process for the synthesis of aryloxypropylamine and heteroaryloxypropylamine of formula I:

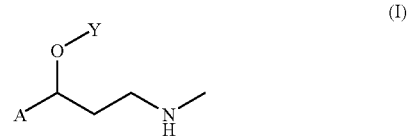

(I)

where: A is aryl or heteroaryl, where the aryl is preferably a phenyl, optionally substituted, selected from benzyl and tolyl and the heteroaryl is preferably thiophenyl; Y is an aryl, preferably phenyl, a substituted phenyl or a naphthyl, where the substituted phenyl is preferably selected from tolyl, trihalomethyltolyl and alkoxytolyl, starting from a suitable amino alcohol of formula II:

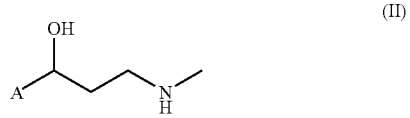

(II)

38 Claims, No Drawings

PROCESS FOR THE SYNTHESIS OF ARYLOXYPROPYLAMINE AND HETEROARYLOXYPROPYLAMINE

CROSS-REFERENCE TO RELATED APPLICATIONS

This application is being filed under Rule 1.371 as a National Stage Application of pending International Application No. PCT/EP2007/060564 filed Oct. 4, 2007, which claims priority to the following parent application: Italian Patent Application No. MI2006A001987, filed Oct. 16, 2006. Both International Application No. PCT/EP2007/060564 and Italian Patent Application No. MI2006A001987 are hereby incorporated by reference herein in their entirety.

FIELD OF THE INVENTION

The present invention is related to a process for the synthesis of aryloxypropylamine and heteroaryloxypropylamine of formula I:

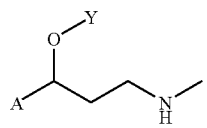

(I)

where:
A is aryl or heteroaryl, where aryl is preferably a phenyl, optionally substituted, selected from benzyl and tolyl and the heteroaryl is preferably thiophenyl; Y is an aryl, preferably phenyl, a substituted phenyl or a naphthyl, where the substituted phenyl is preferably selected from tolyl, trihalomethyltolyl and alkoxytolyl.

BACKGROUND OF THE INVENTION

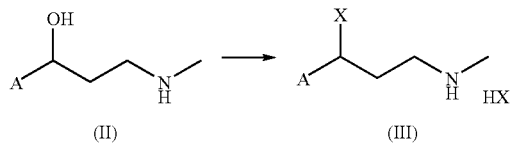

Aryloxypropylamines are an important class of pharmaceutical products used in the care of attention-deficit disorder and hyperactivity disturbances.

Some of the most important products belonging to this class are the following:

Fluoxetine-formula VI

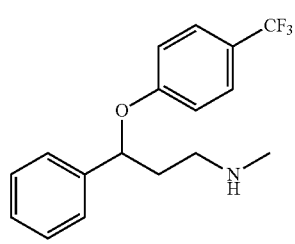

(VI)

Atomoxetine-formula VII

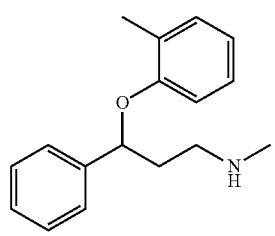

(VII)

Nisoxetine-formula VIII

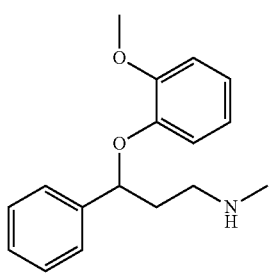

(VIII)

Duloxetine is a chemically very similar product having the following formula:

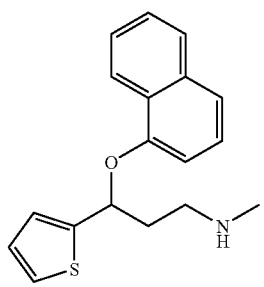

(IX)

It is used as drug for the care of depression and incontinence.

The known synthesis paths for obtaining this product type starting from the corresponding amino alcohol can be divided into two groups:

A) Aromatic nucleophilic substitution processes like those described in WO0058262.

This hind of process provides for the substitution of a halogen atom on the ring by the OH of the amino alcohol of formula II, suitably activated as an alcoholate. This process type is applicable with good results only when electron-attractor groups are present on the aromatic ring which bears the halogen to be substituted (in the diagram below, when A and X have the meanings defined above and Y' is an electron-attractor group).

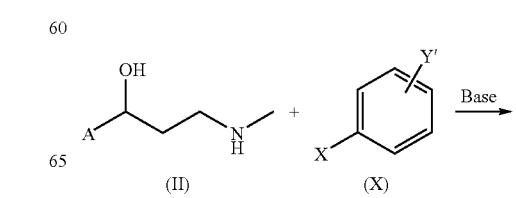

-continued

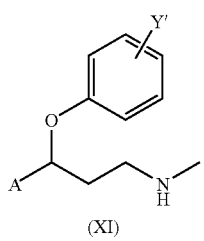

(XI)

B) Nucleophilic substitution reactions of the hydroxyl of the amino alcohol. (see for example U.S. Pat. No. 4,018,895 and U.S. Pat. No. 4,314,081).

This kind of process normally provides for the following reaction sequence:
a) protection of the amino group;
b) activation of the hydroxyl by means of its transformation into a good leaving group (preferably a halogen);
c) nucleophilic substitution with the appropriate aryloxy, optionally substituted;
d) deprotection of the amino group

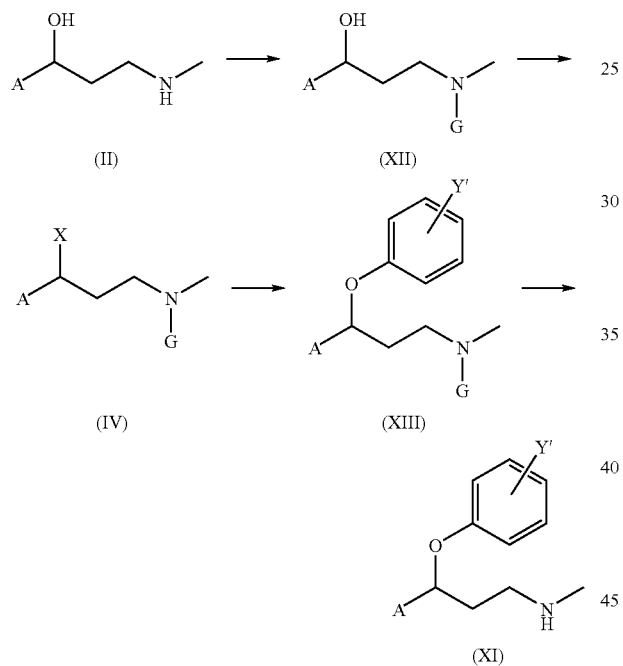

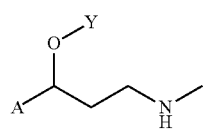

(XI)

The processes of this type are longer but have a much wider range of application.

SUMMARY OF ADVANTAGEOUS EMBODIMENTS OF THE INVENTION

The present invention is related to a process for the synthesis of aryloxypropylamine and heteroaryloxypropylamine of formula I:

(I)

where:
A is aryl or heteroaryl, where aryl is preferably a phenyl, optionally substituted, selected from benzyl and tolyl and the heteroaryl is preferably thiophenyl; Y is an aryl, preferably phenyl, a substituted phenyl or a naphthyl, where the substituted phenyl is preferably selected from tolyl, trihalomethyl-tolyl and alkoxytolyl;
starting from a suitable amino alcohol of formula II:

(II)

in which the hydroxyl is substituted with a halogen to give compounds of formula III, which are obtained as hydrohalogenated salts:

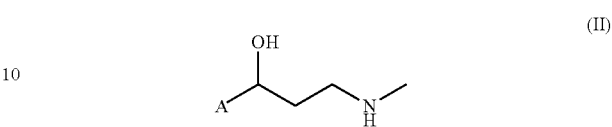

(II)  (III)

The compounds of formula III are reacted with a protective agent of amino groups to give compounds of formula IV

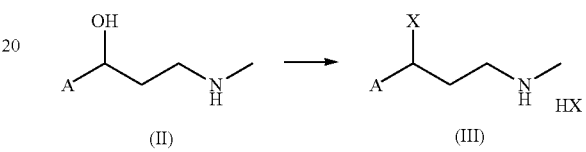

(III)  (IV)

where G indicates a protector group of the amino group, of formula R—C(=O)—, where R is an alkyl, optionally substituted, residue, aryl or alkoxy residue, or of formula R'—S(=O)$_2$— where R' indicates a alkyl residue optionally substituted or aryl residue.

The compounds of formula IV are reacted with the anions of the aryl alcohols of interest, preferably phenols, substituted phenols or naphthols to give the compounds of formula V

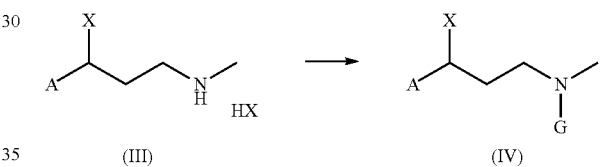

(IV)  (V)

The compounds of formula V are then appropriately deprotected.

DETAILED DESCRIPTION OF ADVANTAGEOUS EMBODIMENTS OF THE INVENTION

During the study of the synthesis of aryloxy and heteroaryloxy propylamine we surprisingly found that if in the processes of B type the order of the amino group protection and hydroxyl activation stages is reversed, greater overall yields are obtained. Moreover, taking into consideration that the activation of the hydroxyl is generally carried out in an acidic environment, reversing the two reaction stages permits using protective groups of the amino group which are not compatible with acidic environments.

The reaction sequence of the present invention is therefore the following:
a) activation of the hydroxyl of an amino alcohol of formula II by means of its substitution with a halogen atom, preferably by means of reaction with a suitable halogenating agent (for example of the type SOX$_2$, PX$_3$, PDX$_3$, etc., where X indicates a halogen), to obtain the salified amino halogen-derivative of formula III.

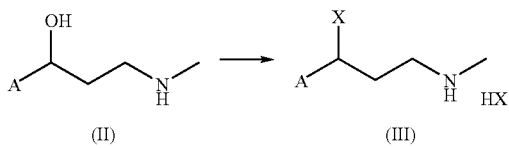

This reaction is carried out in a halogenated solvent, preferably methylene chloride, at a temperature in the range of 0° C.-40° C., preferably in the range of 20° C.-25° C. The quantity of halogenating agent, preferably thionyl chloride, is in the range of 0.8-3 equivalents with respect to the starting amino alcohol, preferably in the range of 1-2 equivalents. The reaction time is in the range of 1-4 hours, preferably in the range of 1-2 hours.
b) protection of the amino group of the amino halogen-derivative of formula III, to obtain the protected amino halogen-derivative of formula IV.

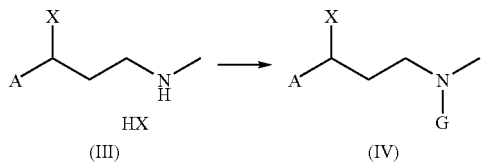

where G is an amino protecting group.

The methods for protecting amines are well known in the art and are described for example in Greene et al., *Protective Groups in Organic Synthesis*, chapter 7, Third Edition, 1999, Wiley-Interscience, pages 494-653, incorporated here for reference.

Preferably, G indicates a protector group of the amino group, preferably of formula R—C(=O)— where R is an alkyl residue, optionally substituted, aryl or alkoxy residue, or of formula R'—S(=O)$_2$— where R' indicates an alkyl, optionally substituted, alkyl residue or aryl residue.

The protection reaction is carried out in a halogenated solvent, preferably methylene chloride, and water, (in ratios in the range of 0.5-1.5 to 1, preferably 0.75 to 1) at a temperature in the range of 0° C.-30° C., preferably in the range of 5° C.-10° C., and in the presence of a base. The quantity of protective agent, which can be an activated derivative of an acyl, preferably an acetyl or a benzoyl, of a sulfonyl, preferably a tosyl, or of an oxyformyl, preferably a benzyloxyformyl or an ethoxyformyl, is in the range of 0.8-3 equivalents with respect to the starting amino halogen-derivative, preferably in the range of 1-2 equivalents. The quantity of base, preferably NaOH, is in the range of 1-4 equivalents with respect to the starting amino halogen-derivative, preferably in the range of 2-3 equivalents. The reaction time is in the range of 1-4 hours, preferably 1-2 hours.
c) substitution of the halogen of the protected amino halogen-derivative of formula IV with the appropriate aryloxy, so to obtain the protected aryloxypropylamine (or heteroaryloxypropylamine) of formula XIII.

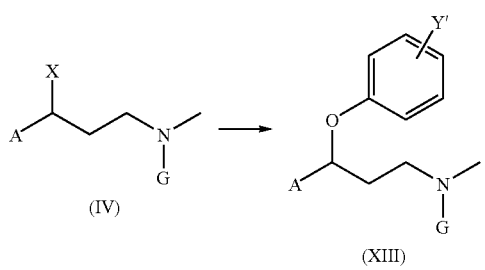

This reaction is carried out in an ether solvent, preferably polar, still more preferably tetrahydrofuran, at a temperature in the range of 25° C.-65° C., preferably 50° C.-65° C. The quantity of aryloxy, preferably obtained from o-cresol by means of a base, is in the range of 1-5 equivalents with respect to the starting protected amino halogen-derivative, preferably in the range of 2-4 equivalents. The quantity of base, preferably KOH, is in the range of 1-5 equivalents with respect to the starting protected amino halogen-derivative, preferably in the range of 2-4 equivalents. The reaction time is in the range of 5-20 hours, preferably in the range of 10-12 hours.
d) Deprotection of the formula compounds (XIII) to obtain the aryloxypropanolamine or heteroaryloxypropylamine of the invention, of formula (XI).

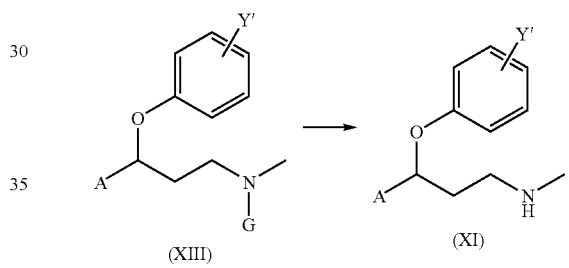

The deprotection reaction type to be used varies in relation to the protective group and is well known in the art (see Greene et al. above). In the case of amides or carbamates, hydrolysis reactions in basic environment are used.

If the carbamate is a benzylcarbamate, catalytic hydrogenolysis reactions are preferably utilised for the deprotection. Such hydrogenolysis reactions can be conducted with hydrogen, formic acid, ammonium formate, tertiary amine salts with formic acid or mixtures of formic acid and its salts.

The invention will be further illustrated by the following examples, which should not be considered as limiting the object of the invention.

Stage a) —Activation of the Hydroxyl

Preparation of a Compound of Formula III

Example 1

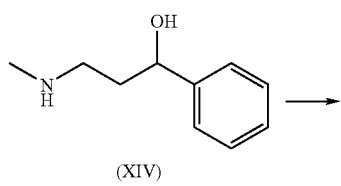

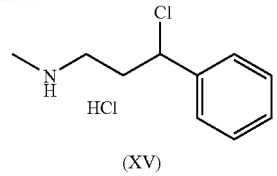

(XV)

N-methyl-3-phenyl-3-hydroxy-propylamine (100 g; 0.60 moles) is loaded while being stirred at room temperature into methylene chloride (400 ml), obtaining a solution. A solution of $SOCl_2$ (52.7 ml; 0.73 moles) is dripped in about 30 minutes into methylene chloride (100 ml), and the resulting liquid is stirred at room temperature for 1-2 h. The vacuum solvent is evaporated at 40° C. until a solid residue is attained. Acetone (400 ml) is added; the suspension is left to stir for 30 minutes and the solvent is removed by vacuum evaporation. Acetone (500 ml) is once again added; the suspension is reflux heated (56° C.) for 1 h, then it is cooled to room temperature and left stirring for 1 h. The solid is filtered, washing the panel with acetone (100 ml) and it is dried in a 50° C. oven so to obtain the compound of formula XV (117.6 g; 88% yield).

Stage b) —Protection of the Amino Group
Preparation of a Compound of Formula IV

The protection of the amino group of the compounds of formula III can be carried out in different modes known in the art. Several of these are illustrated in examples 2-7.

Diagram of Examples 2-3

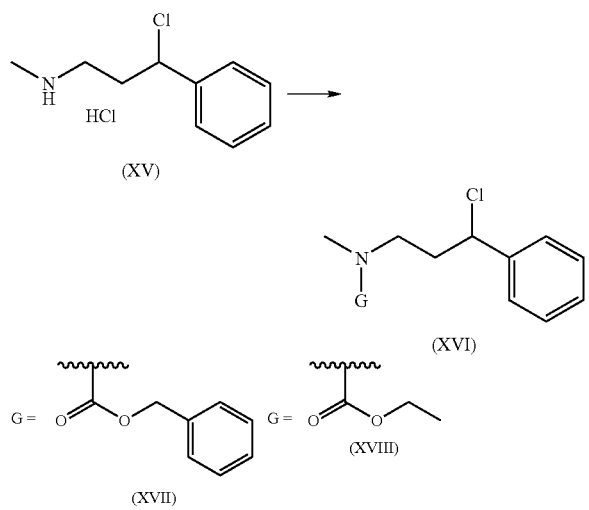

Example 2

Compound of Formula XVII (G=Benzyloxyformyl)

NaOH (63.8 g; 1.59 moles) is loaded at 5/10° C. into $H_2O$ (800 ml). Ethyl acetate is added (585 ml). The compound of formula XV is loaded (117 g; 0.53 moles) and finally, in about 1 h and still at 5/10° C., the benzyl chloroformate (83.5 ml; 0.58 moles) is loaded. The resulting mixture is stirred at 5/10° C. for 2-3 h. The 2 phases are separated; the organic phase is vacuum evaporated to form an oily residue (compound of formula XVII; 191 g; 94% yield), which is used as is for the subsequent step (see example 8).

Example 3

Compound of Formula XVIII (G=Ethoxyformyl)

In an analogous manner, the compound of formula XVIII (which is used for such for the subsequent step, see example 8) is prepared by using ethyl chloroformate.

Diagram of Examples 4-6

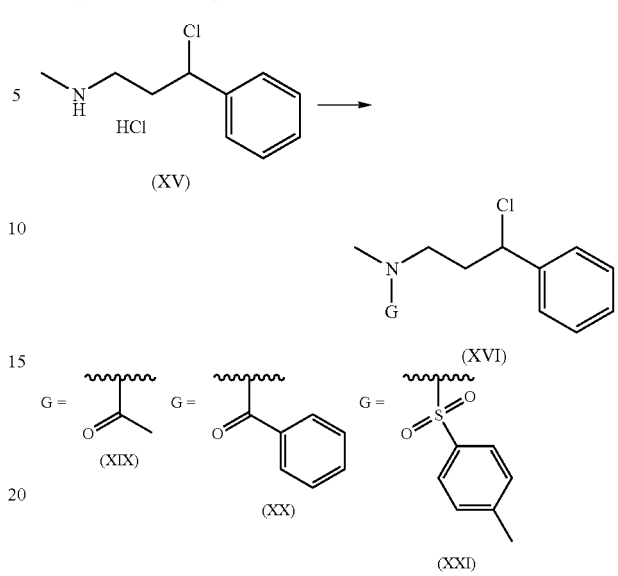

Example 4

Compounds of Formula XIX (G=Acetyl)

The compound XV (55 g; 0.25 moles) is loaded at room temperature into methylene chloride (550 ml) and triethylamine (83 ml; 0.6 moles). Acetyl chloride (21.3 ml; 0.3 moles) is added, still at room temperature and in about 30 minutes. The resulting mixture is stirred at room temperature for 1 h. $H_2O$ (200 ml) is added and the 2 phases are separated; the organic phase is vacuum evaporated to form an oily residue (compound XIX); 55 g; 97% yield), which is used as is for the subsequent step (see example 8).

Example 5

Compound of Formula XX (G=Benzoyl)

In an analogous manner, the compound of formula XX is prepared (which is used as is for the subsequent step, see example 8) by utilising benzoyl chloride.

Example 6

Compound of Formula XXI (G=Tosyl)

In an analogous manner, the compound of formula XXI (which is used as is for the subsequent step, see example 8) is prepared by using tosyl chloride.

Diagram of Example 7

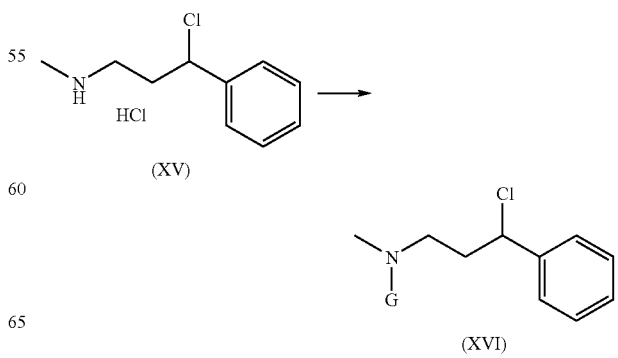

-continued

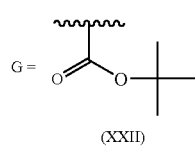

(XXII)

Example 7

Compound of Formula XXII (G=t-Butoxyformyl)

H₂O (135 ml) and 30% NaOH (30 ml; 0.3 moles) are mixed at room temperature. The compound of formula XV (30 g; 0.14 moles) and t-BuOH (135 ml) are added. Finally, Boc₂O (32.7 g; 0.15 moles) is loaded to portions in about 30 minutes. The resulting mixture is stirred at room temperature for 1 h. The 2 phases are separated; the organic phase is vacuum evaporated to form an oily residue (compound of formula XXII; 35 g; 90% yield), which is utilised as such for the subsequent step (see example 8).

Stage c) —Substitution

Preparation of a Compound of Formula V

Example 8

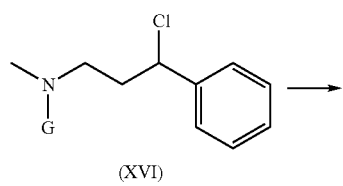

KOH (135.9 g; 2.18 moles) is loaded at room temperature into THF (420 ml), and this is heated to 50/60° C. O-cresol (230 g; 2.13 moles) is added into THF (230 ml). The resulting mixture is stirred at 50/60° C. for 1 h, then a solution of compound XVI (168 g; 0.53 mol) is added into THF (170 ml). The reaction mixture is reflux heated (66° C.), and stirred for 12 h. It is cooled to room temperature; the THF is evaporated, toluene (400 ml) and 10% NaOH (100 ml) are added; the 2 phases are separated; the organic phase is washed with 10% NaOH (2*100 ml). The combined organic phases are vacuum evaporated to form a small residue. Methanol (250 ml) is added at 50/60° C., and the resultant is cooled at 0/5° C. for 2-3 h. Filtering is then carried out, washing the panel with methanol (50 ml), and the solid is vacuum dried at 50'C to obtain the compound XXIII (154 g; 74.4% yield).

Stage d) —Deprotection

Preparation of a Compound of Formula VII

Example 9

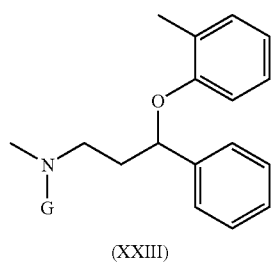

The compound of formula VII is obtained from the compound of formula XXIII, by means of methods known in literature.

Example 10

Compound of Formula XXIV

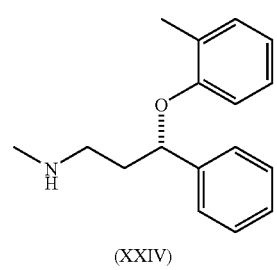

The compound of formula XXIV is obtained from the compound VII, by means of methods known in literature.

The invention claimed is:
1. Process for the synthesis of compounds of formula I

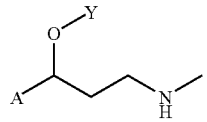 (I)

where:
A is phenyl, benzyl, tolyl or thiophenyl,
Y is phenyl, tolyl, trihalomethyltolyl, alkoxytolyl or naphtyl,
comprising the following stages:
a) halogenating an amino alcohol of formula II:

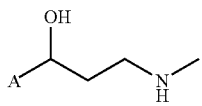 (II)

where A has the foregoing meanings, in order to obtain the salified amino halogen-derivative of formula III:

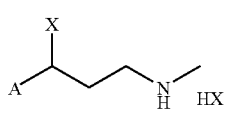 (III)

where X represents a halogen;
b) protecting the amino group of the salified amino halogen-derivative of formula III with a protective agent of the amino groups, in order to obtain the compound of formula IV

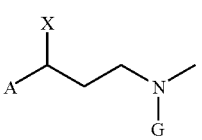 (IV)

where A and X have the foregoing meanings and G indicates a protector group of the amino groups having formula R—C(=O)—, where R is an alkyl residue, aryl residue or alkoxy residue, or having formula R'—S(=O)$_2$—, where R' indicates an alkyl residue or aryl residue;
c) performing a substitution reaction on the protected amino halogen-derivative of formula IV by the anion of an aryl alcohol of formula Y—OH, where Y has the foregoing meanings, to give the protected aryloxypropylamine or heteroaryloxypropylamine of formula V; and

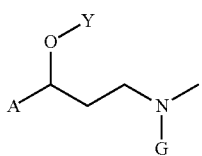 (V)

d) deprotecting the amino group.

2. Process according to claim 1, wherein said halogenating comprises a halogenation agent.
3. Process according to claim 2, wherein the halogenating agent comprises SOX$_2$, PX$_3$, or POX$_3$, where X is a halogen having the foregoing meaning.
4. Process according to claim 2 wherein the halogenation agent is thionyl chloride.
5. Process according to claim 2, wherein the quantity of halogenating agent is in the range of 0.8-3 equivalents with respect to the starting amino alcohol of formula II.
6. Process according to claim 1, wherein the reaction time of stage a) is in the rouge of 1-4 hours.
7. Process according to claim 1, wherein the temperature of the reaction stage a) is in the range of 0°-40° C.
8. Process according to claim 1, wherein the reaction of stage a) is conducted in the presence of a halogenated solvent.
9. Process according to claim 1, wherein the reaction of stage b) occurs in the presence of a base.
10. Process according to claim 9, wherein the base utilized in the reaction stage b) is NaOH.
11. Process according to claim 1, wherein the reaction stage b) is carried out in the presence of a halogenated solvent and water.
12. Process according to claim 1, wherein the protective agent of stage b) is benzyl chloroformate.
13. Process according to claim 1, wherein the quantity of the protective agent utilized in stage b) in order to obtain the compound of formula IV is in the range of 0.8-3 equivalents with respect to the amino halogen-derivative of formula III.
14. Process according to claim 1, wherein the quantity or base utilized in stage b) is in the range of 1-4 equivalents with respect to the starting amino halogen-derivative III.
15. Process according to claim 1, wherein the reaction time of stage b) is in the range of 1-4 hours.
16. Process according to claim 1, wherein the temperature of the reaction stage b) is in the range of 0° C.-30° C.
17. Process according to claim 1, wherein the anion of the aryl alcohol of formula Y—OH is obtained by means of the action of a base.
18. Process according to claim 1, wherein the reaction of stage c) is conducted in the presence of an ether solvent.
19. Process according to claim 1, wherein the base utilized in stage c) is KOH.
20. Process according to claim 1, wherein the quantity of base is in the range of 1-5 equivalents with respect to the protected amino halogen-derivative of Formula IV.
21. Process according to claim 1, wherein the reaction time of stage c) is in the range of 5-20 hours.
22. Process according to claim 1, wherein the temperature of the reaction stage c) is in the range of 25° C.-65° C.
23. Process according to claim 1, wherein the deprotecting stage d) comprises a hydrolysis reaction in a basic environment or a catalytic hydrogenolysis reaction.
24. Process according to claim 23, wherein the catalytic hydrogenolysis reaction is conducted with hydrogen, formic acid, ammonium formate, tertiary amine sails with formic acid or mixtures of formic acid and its salts.
25. Process according to claim 5, wherein the quantity of halogenation agent is in the range of 1-2 equivalents with respect to the starting amino alcohol of formula II.
26. Process according to claim 1, wherein she reaction time of stage a) is in the range of 1-2 hours.
27. Process according to claim 1, wherein the temperature of the reaction stage a) is in the range of 20° C.-25° C.
28. Process according to claim 1, wherein the reaction of stage a) is conducted in the presence of methylene chloride.

29. Process according to claim 1, wherein the reaction stage b) is carried out in the presence of methylene chloride and water.

30. Process according to claim 1, wherein the quantity of the protective agent utilized in stage b) in order to obtain the compound of formula IV is in the range of 1-2 equivalents with respect to the amino halogen-derivative of formula III.

31. Process according to claim 1, wherein the quantity of base utilized in stage b) is in the range of 2-3 equivalents with respect to the starting amino halogen-derivative III.

32. Process according to claim 1, wherein the reaction time of stage b) is in the range of 1-2 hours.

33. Process according to claim 1, wherein the temperature of the reaction stage b) is in the range of 5° C.-10° C.

34. Process according to claim 1, wherein the reaction of stage c) is conducted in the presence of an ether solvent which is polar.

35. Process according to claim 1, wherein the reaction of stage c) is conducted in the presence of tetrahydrofuran.

36. Process according to claim 1, wherein the quantity of base is in the range of 2-4 equivalents with respect to the protected amino halogen-derivative of formula IV.

37. Process according to claim 1, wherein the reaction time of stage c) is in the range of 10-12 hours.

38. Process according to claim 1, wherein the temperature of the reaction stage c) is in the range of 50° C.-65° C.

* * * * *

UNITED STATES PATENT AND TRADEMARK OFFICE
CERTIFICATE OF CORRECTION

PATENT NO. : 8,367,868 B2  Page 1 of 1
APPLICATION NO. : 12/444710
DATED : February 5, 2013
INVENTOR(S) : Bertolini et al.

It is certified that error appears in the above-identified patent and that said Letters Patent is hereby corrected as shown below:

Claims

Column 12

Claim 6, Line 12, delete "rouge" and insert --range--

Claim 14, Line 30, delete "or" and insert --of--

Claim 26, Line 62, delete "she" and insert --the--

Signed and Sealed this
Ninth Day of April, 2013

Teresa Stanek Rea
*Acting Director of the United States Patent and Trademark Office*